United States Patent
Molaei et al.

(10) Patent No.: US 10,383,644 B2
(45) Date of Patent: Aug. 20, 2019

(54) MECHANICAL THROMBECTOMY WITH PROXIMAL OCCLUSION

(71) Applicant: Covidien LP, Mansfield, MA (US)

(72) Inventors: Masoud Molaei, Laguna Niguel, CA (US); Evan David Epstein, Los Angeles, CA (US); Garrett Johnson, Costa Mesa, CA (US); Ghislain Sema, Slidell, LA (US)

(73) Assignee: Covidien LP, Mansfield, MA (US)

( * ) Notice: Subject to any disclaimer, the term of this patent is extended or adjusted under 35 U.S.C. 154(b) by 620 days.

(21) Appl. No.: 14/056,461

(22) Filed: Oct. 17, 2013

(65) Prior Publication Data

US 2015/0112376 A1    Apr. 23, 2015

(51) Int. Cl.
  *A61F 2/01*      (2006.01)
  *A61B 17/12*     (2006.01)
  (Continued)

(52) U.S. Cl.
  CPC ...... *A61B 17/221* (2013.01); *A61B 17/12022* (2013.01); *A61B 17/22031* (2013.01);
  (Continued)

(58) Field of Classification Search
  CPC ...... A61F 2/013; A61F 2/01; A61F 2002/016; A61F 2002/018; A61F 2002/011;
  (Continued)

(56) References Cited

U.S. PATENT DOCUMENTS

| 4,611,594 A | 9/1986 | Grayhack |
| 5,011,488 A | 4/1991 | Ginsburg |

(Continued)

FOREIGN PATENT DOCUMENTS

| CN | 101340849 A | 1/2009 |
| CN | 102014772 A | 4/2011 |

(Continued)

OTHER PUBLICATIONS

U.S. Appl. No. 13/609,777, filed Sep. 11, 2012.

*Primary Examiner* — Katrina M Stransky
(74) *Attorney, Agent, or Firm* — Fortem IP LLP; Mary Fox

(57) ABSTRACT

The medical device can comprise a manipulation member, a mechanical thrombectomy apparatus attached to a distal end of the manipulation member, and flow-restricting apparatus attached to the manipulation member to a location proximal to the mechanical thrombectomy apparatus. A method, for retrieving thrombus from a blood vessel, can comprise advancing a single elongate delivery member carrying a mechanical thrombectomy apparatus and a flow-restricting apparatus through a catheter to the blood vessel, expanding the thrombectomy apparatus and capturing the thrombus with the thrombectomy device, expanding the flow-restricting apparatus to at least partially occlude blood flow toward the thrombus, retracting at least a portion of the thrombectomy apparatus into the flow-restricting apparatus, and retracting the flow-restricting apparatus and the thrombectomy apparatus into the retrieval catheter.

17 Claims, 8 Drawing Sheets

(51) Int. Cl.
*A61B 17/22* (2006.01)
*A61B 17/221* (2006.01)
*A61B 17/3207* (2006.01)

(52) U.S. Cl.
CPC .......... *A61F 2/013* (2013.01); *A61B 17/1204* (2013.01); *A61B 17/320725* (2013.01); *A61B 2017/2215* (2013.01); *A61B 2017/22034* (2013.01); *A61B 2017/22035* (2013.01); *A61B 2017/22094* (2013.01)

(58) Field of Classification Search
CPC ............ A61B 17/221; A61B 17/22031; A61B 17/12022; A61B 17/1204; A61B 17/320725; A61B 2017/22034; A61B 2017/22035; A61B 2017/2215; A61B 2017/22094; A61B 17/32056; A61B 2017/320716

See application file for complete search history.

(56) References Cited

U.S. PATENT DOCUMENTS

| | | | |
|---|---|---|---|
| 5,102,415 | A | 4/1992 | Guenther et al. |
| 5,549,626 | A | 8/1996 | Miller et al. |
| 5,713,853 | A | 2/1998 | Clark et al. |
| 5,846,251 | A | 12/1998 | Hart |
| 5,971,938 | A | 10/1999 | Hart et al. |
| 6,245,088 | B1 | 6/2001 | Lowery |
| 6,605,102 | B1 | 8/2003 | Mazzocchi et al. |
| 6,638,293 | B1 | 10/2003 | Makower et al. |
| 6,663,650 | B2 | 12/2003 | Sepetka et al. |
| 6,682,543 | B2 | 1/2004 | Barbut et al. |
| 6,702,830 | B1 | 3/2004 | Demarais et al. |
| 6,824,545 | B2 | 11/2004 | Sepetka et al. |
| 7,285,126 | B2 | 10/2007 | Sepetka et al. |
| 7,300,429 | B2 | 11/2007 | Fitzgerald et al. |
| 7,399,308 | B2 | 7/2008 | Borillo et al. |
| 7,727,242 | B2 | 6/2010 | Sepetka et al. |
| 7,766,921 | B2 | 8/2010 | Sepetka et al. |
| 7,837,702 | B2 | 11/2010 | Bates |
| 7,846,175 | B2 | 12/2010 | Bonnette et al. |
| 8,252,017 | B2 | 8/2012 | Paul, Jr. et al. |
| 8,298,257 | B2 | 10/2012 | Sepetka et al. |
| 8,343,170 | B2 | 1/2013 | Massicotte et al. |
| 8,784,441 | B2 | 7/2014 | Rosenbluth et al. |
| 8,795,305 | B2 | 8/2014 | Martin et al. |
| 2001/0037126 | A1 | 11/2001 | Stack et al. |
| 2003/0163158 | A1 | 8/2003 | White |
| 2004/0073243 | A1 | 4/2004 | Sepetka et al. |
| 2005/0159770 | A1 | 7/2005 | Divani et al. |
| 2005/0187570 | A1 | 8/2005 | Nguyen et al. |
| 2006/0195137 | A1* | 8/2006 | Sepetka ................. A61B 17/22 606/200 |
| 2006/0282116 | A1 | 12/2006 | Lowe et al. |
| 2009/0043330 | A1 | 2/2009 | To |
| 2009/0054918 | A1 | 2/2009 | Henson |
| 2009/0198269 | A1* | 8/2009 | Hannes ................ A61B 17/221 606/200 |
| 2010/0030256 | A1 | 2/2010 | Dubrul et al. |
| 2010/0191272 | A1 | 7/2010 | Keating |
| 2010/0211156 | A1 | 8/2010 | Linder et al. |
| 2011/0009941 | A1 | 1/2011 | Grandfield et al. |
| 2011/0060212 | A1 | 3/2011 | Slee et al. |
| 2011/0077680 | A1 | 3/2011 | Heuser |
| 2011/0160762 | A1 | 6/2011 | Hogendijk et al. |
| 2011/0213290 | A1 | 9/2011 | Chin et al. |
| 2011/0218560 | A1 | 9/2011 | Ramzipoor et al. |
| 2011/0288529 | A1 | 11/2011 | Fulton |
| 2012/0059356 | A1* | 3/2012 | di Palma .............. A61B 17/221 604/509 |
| 2013/0030461 | A1 | 1/2013 | Marks et al. |
| 2013/0253569 | A1 | 9/2013 | Sepetka et al. |
| 2014/0155980 | A1* | 6/2014 | Turjman .......... A61B 17/12031 623/1.12 |
| 2014/0277013 | A1 | 9/2014 | Sepetka et al. |

FOREIGN PATENT DOCUMENTS

| | | |
|---|---|---|
| CN | 103110446 A | 5/2013 |
| DE | 102011100733 A1 | 11/2012 |
| DE | 102011100733 A1 | 11/2012 |
| EP | 2158858 | 3/2010 |
| WO | 2006048314 A1 | 5/2006 |
| WO | WO-2006/048314 A1 | 5/2006 |
| WO | 2007068424 A2 | 6/2007 |
| WO | WO-2007/068424 A2 | 6/2007 |
| WO | 2009105710 A1 | 8/2009 |
| WO | WO-2009/105710 A1 | 8/2009 |
| WO | WO-2012/09675 | 1/2012 |

\* cited by examiner

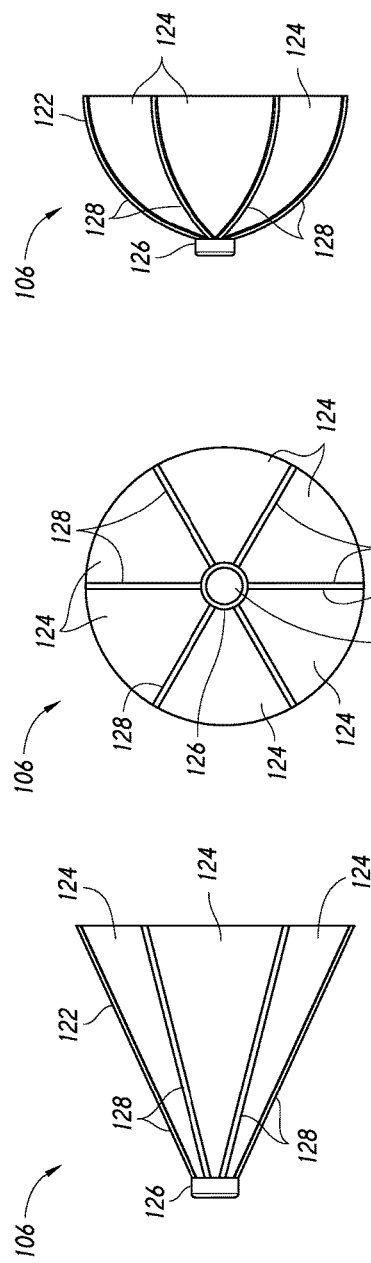
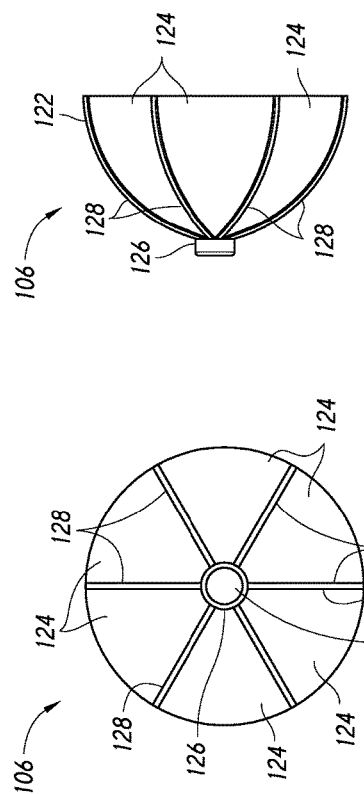
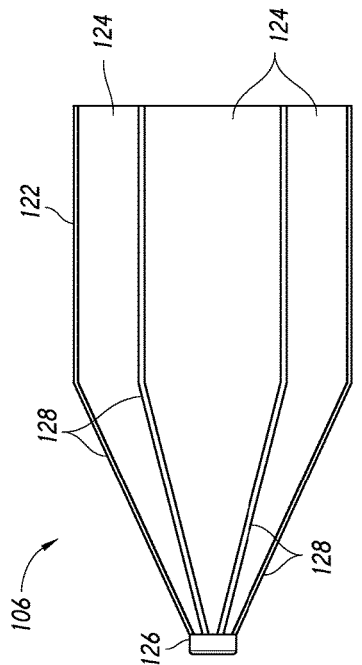
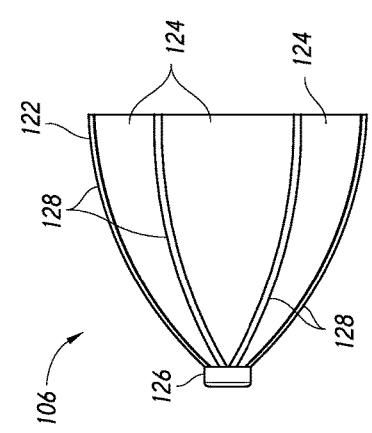
FIG. 2A
FIG. 2B
FIG. 3
FIG. 4
FIG. 5

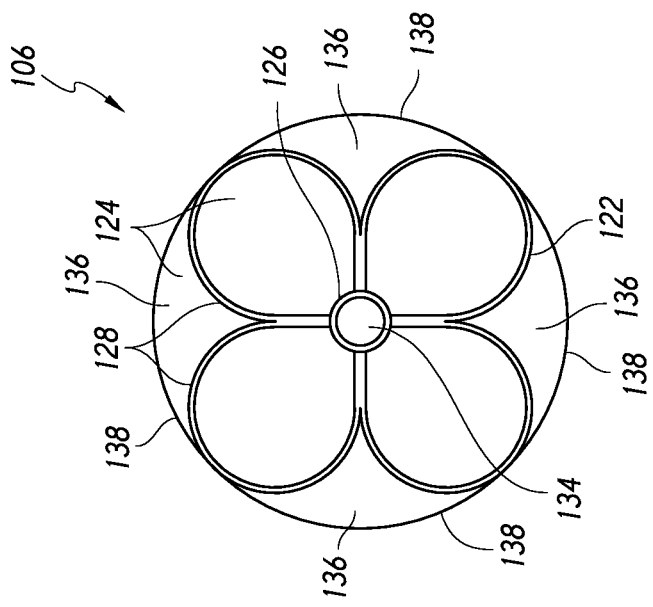
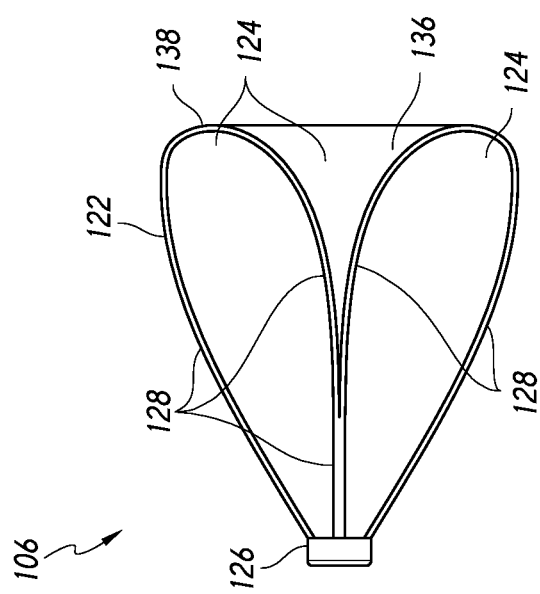

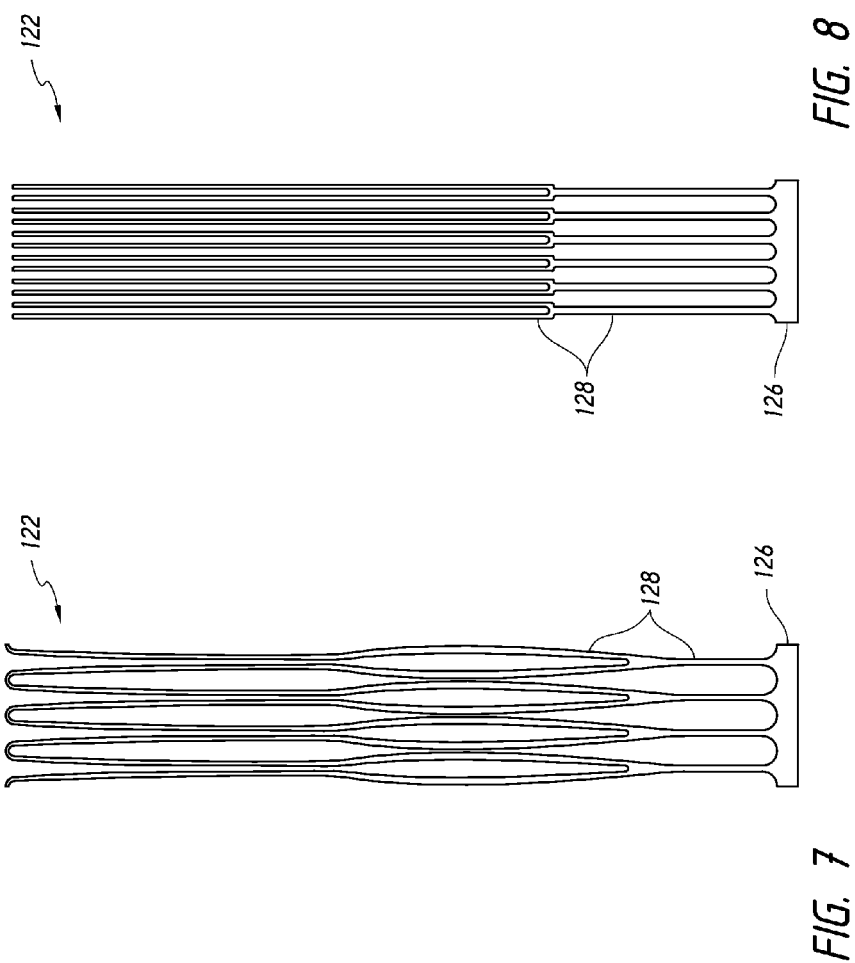

MECHANICAL THROMBECTOMY WITH PROXIMAL OCCLUSION

BACKGROUND

Blood vessels can become occluded by emboli, e.g., thrombi. For example, intracranial arteries can become occluded by thromboembolisms. Disruption of blood flow by the occlusion can prevent oxygen and nutrients from being delivered to tissues downstream of the occlusion. Deprivation of oxygen and nutrients to tissue distal to an occlusion can impair proper function of the tissue, and may result in cellular death. Cellular death increases with duration of the occlusion.

SUMMARY

Acute ischemic stroke can be treated by removal of an occlusive thrombus using a mechanical thrombectomy device. The efficacy of such procedures can be improved by occluding blood flow, applying aspiration, or both at a location proximal to the thrombus during removal of the thrombus to eliminate distally directed blood flow, which would oppose thrombus removal. By reducing or eliminating distally directed blood flow, the efficacy of thrombus retrieval can be improved. Blood flow can be occluded by inflating the balloon of balloon catheter at a location proximal to the thrombus. The outer diameters of guide catheters through which aspiration is applied and balloon catheters typically prevent them from being advanced into close proximity of the thrombus, which frequently become lodged in small intracranial vessels. An aspect of at least some of the embodiments disclosed herein involves the recognition that the distance separating the thrombus from the location of balloon inflation or the distal end of a catheter through which aspiration is applied undesirably deprives the intervening region of the brain of blood during at least a portion of the procedure. A flow-restricting apparatus can be used to occlude or reduce distally directed blood flow at a location proximal to and in close proximity to the thrombus to improve efficacy of thrombus retrieval while diminishing the area of blood flow deprivation during thrombus retrieval compared to use of a balloon catheter or aspiration. In some instances, the disclosed devices including flow-restricting apparatuses and associated methods of use can allow a balloon or other guide catheter to be omitted from the mechanical thrombectomy procedure.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., Clause 1 or Clause 20. The other clauses can be presented in a similar manner.

Clause 1. A method for retrieving thrombus from a blood vessel, the method comprising:
advancing a distal end of a delivery catheter to the blood vessel;
advancing a single elongate delivery member carrying a mechanical thrombectomy device and an flow-restricting device through the delivery catheter to the blood vessel with the flow-restricting device proximal to the thrombectomy device;
expanding the thrombectomy device and capturing the thrombus with the thrombectomy device;
expanding the flow-restricting device to at least partially occlude blood flow toward the thrombus;
retracting at least a portion of the thrombectomy device into the flow-restricting device; and
retracting the flow-restricting device and the thrombectomy device into the retrieval catheter.

Clause 2. The method of Clause 1, further comprising inserting a guide wire through the thrombus, and advancing the distal end of a delivery catheter over the guide wire to the blood vessel.

Clause 3. The method of Clause 1, wherein advancing the distal end of a delivery catheter to the blood vessel comprises advancing the distal end of a delivery catheter to within 3 cm of the thrombus.

Clause 4. The method of Clause 1, wherein advancing the distal end of a delivery catheter to the blood vessel comprises advancing the distal end of a delivery catheter to a location distal to a distal end of the thrombus.

Clause 5. The method of Clause 1, wherein advancing the single elongate delivery member comprises positioning a distal end of the thrombectomy device distal to the thrombus and a proximal end of the thrombectomy device proximal to the thrombus.

Clause 6. The method of Clause 5, wherein the thrombectomy device is expanded into the thrombus.

Clause 7. The method of Clause 1, wherein the flow-restricting device is maintained within the delivery catheter while expanding the thrombectomy device.

Clause 8. The method of Clause 1, further comprising waiting for a period of at least 30 seconds after expanding of the thrombectomy device before expanding of the flow-restricting device.

Clause 9. The method of Clause 1, wherein the flow-restricting device is expanded after expanding the thrombectomy device.

Clause 10. The method of Clause 1, further comprising retracting at least a portion of the thrombus into the flow-restricting device.

Clause 11. The method of Clause 1, wherein retracting at least a portion of the thrombectomy device into the flow-restricting device comprises retracting the thrombectomy device until a stop member abuts a portion of the flow-restricting device.

Clause 12. The method of Clause 1, further comprising retracting the flow-restricting device and the thrombectomy device together toward the distal end of the delivery catheter.

Clause 13. The method of Clause 1, further comprising retracting the flow-restricting device, the thrombectomy device, and the delivery catheter together toward the retrieval catheter.

Clause 14. The method of Clause 1, further comprising inflating a balloon on the retrieval catheter.

Clause 15. The method of Clause 14, further comprising inflating the balloon before retracting the flow-restricting device into the retrieval catheter, Clause 16. The method of Clause 14, further comprising inflating the balloon after retracting the flow-restricting device into the retrieval catheter.

Clause 17. The method of Clause 14, further comprising, before inflating the balloon, retracting the flow-restricting device, with the thrombectomy device, toward the retrieval catheter until the flow-restricting device is within 1 cm of a distal end of the retrieval catheter.

Clause 18. The method of Clause 1, further comprising aspirating through the retrieval catheter while retracting at least one of the thrombus, the flow-restricting device, or the thrombectomy device into the retrieval catheter.

Clause 19. The method of Clause 1, further comprising containing at least a portion of at least one of the thrombus and thrombectomy device with the flow-restricting device while retracting the flow-restricting device and the thrombectomy device into the retrieval catheter.

Clause 20. A thrombectomy device, comprising:
an elongate delivery member;
a first expandable member attached to the elongate delivery member at a distal end of the elongate delivery member, and configured to capture a thrombus, the first expandable member having an expanded configuration and a collapsed configuration, the first expandable member having a maximum transverse outer dimension that is larger in the expanded configuration than in the collapsed configuration; and
a second expandable member slidably attached to the elongate delivery member at a location proximal to the first expandable member, and comprising a hub slidably surrounding the elongate delivery member, an expandable frame extending from the hub, and a membrane attached to the expandable frame, the hub having a static transverse inner dimension that is smaller than the maximum transverse outer dimension of the first expandable member in the collapsed configuration, the expandable frame having an expanded frame configuration and a collapsed frame configuration, the expandable frame having a maximum transverse outer frame dimension that is larger in the expanded frame configuration than in the collapsed frame configuration, the membrane extending from the hub to an outermost circumferential perimeter of the expandable frame in the expanded frame configuration.

Clause 21. The thrombectomy device of Clause 20, wherein the first expandable member is configured to integrate with a thrombus upon expansion of the first expandable member.

Clause 22. The thrombectomy device of Clause 20, wherein the first expandable member comprises a plurality of cells and, in the expanded configuration of the first expandable member, is generally tubular and has an open proximal end and an open distal end.

Clause 23. The thrombectomy device of Clause 20, wherein the frame comprises a proximal portion and a distal portion, the distal portion being cylindrical in the expanded configuration, and the proximal portion flaring from the hub to the distal portion.

Clause 24. The thrombectomy device of Clause 20, wherein the membrane extends from the hub along the entire longitudinal extent of the expandable frame.

Clause 25. The thrombectomy device of Clause 20, further comprising a first stop member fixed to the elongate delivery member proximal to a proximal end of the second expandable member.

Clause 26. The thrombectomy device of Clause 25, wherein the first stop member has a maximum transverse outer dimension that is larger than the transverse inner dimension of the hub.

Clause 27. The thrombectomy device of Clause 25, wherein the first stop member comprises radiopaque material.

Clause 28. The thrombectomy device of Clause 25, further comprising a second stop member fixed to the elongate delivery member distal to the second expandable member.

Clause 29. The thrombectomy device of Clause 28, wherein, in the collapsed frame configuration, a portion comprising a distal end of the frame has a minimum transverse inner dimension smaller than a maximum transverse outer dimension the second stop member.

Clause 30. The thrombectomy device of Clause 28, wherein the second stop member has a maximum transverse outer dimension that is larger than the transverse inner dimension of the hub.

Clause 31. The thrombectomy device of Clause 28, wherein the second stop member comprises radiopaque material.

Clause 32. The thrombectomy device of Clause 28, wherein the first stop member and the second stop member are separated by a distance greater than a length of the second expandable member when the frame is in the collapsed frame configuration.

Clause 33. The thrombectomy device of Clause 20, wherein the second expandable member is self-expandable.

Clause 34. The thrombectomy device of Clause 20, wherein the hub has a length less than 1 cm.

Clause 35. The thrombectomy device of Clause 20, wherein the hub of the second expandable member comprises a circumferentially contiguous metallic tube having a length less than 1 cm.

Clause 36. The thrombectomy device of Clause 20, wherein the membrane is attached on a radially outwardly facing surface of the frame.

Clause 37. The thrombectomy device of Clause 20, wherein the frame comprises a first plurality of struts and a second plurality of struts, each strut of the first plurality has a proximal end connected to the hub and a distal end connected to at least two struts of the second plurality, each strut of the second plurality has a first and second ends connected to adjacent struts of the first plurality.

Clause 38. The thrombectomy device of Clause 20, wherein the second expandable member comprises means for containing at least a portion of at least one of the thrombus and the first expandable member during retrieval of the thrombectomy device.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this description, illustrate aspects of the subject technology and, together with the specification, serve to explain principles of the subject technology.

FIGS. 2A and 2B are a side view and an end view, respectively, of a flow-restricting apparatus with a frusto-conical portion, according to an embodiment.

FIG. 3 is a side view of a flow-restricting apparatus with a hemispherical portion, according to an embodiment.

FIG. 4 is a side view of a flow-restricting apparatus with a hemiovoid portion, according to an embodiment.

FIG. 5 is a side view of a flow-restricting apparatus with a frustoconical portion and a cylindrical portion, according to an embodiment.

FIGS. 6A and 6B are a side view and an end view, respectively, of a flow-restricting apparatus comprising a frame and a cover, according to an embodiment.

FIG. 7 is a plan view of the frame of FIGS. 6A and 6B, according to an embodiment.

FIG. 8 is a plan view of a frame for a flow-restricting apparatus, according to an embodiment.

DETAILED DESCRIPTION

The detailed description set forth below is intended as a description of various configurations of the subject technology and is not intended to represent the only configurations in which the subject technology may be practiced. The detailed description includes specific details for the purpose of providing a thorough understanding of the subject technology. However, the subject technology may be practiced without these specific details. In some instances, well-known structures and components are not shown, or are shown schematically or in block diagram form, to avoid obscuring the concepts of the subject technology.

Figure 1:
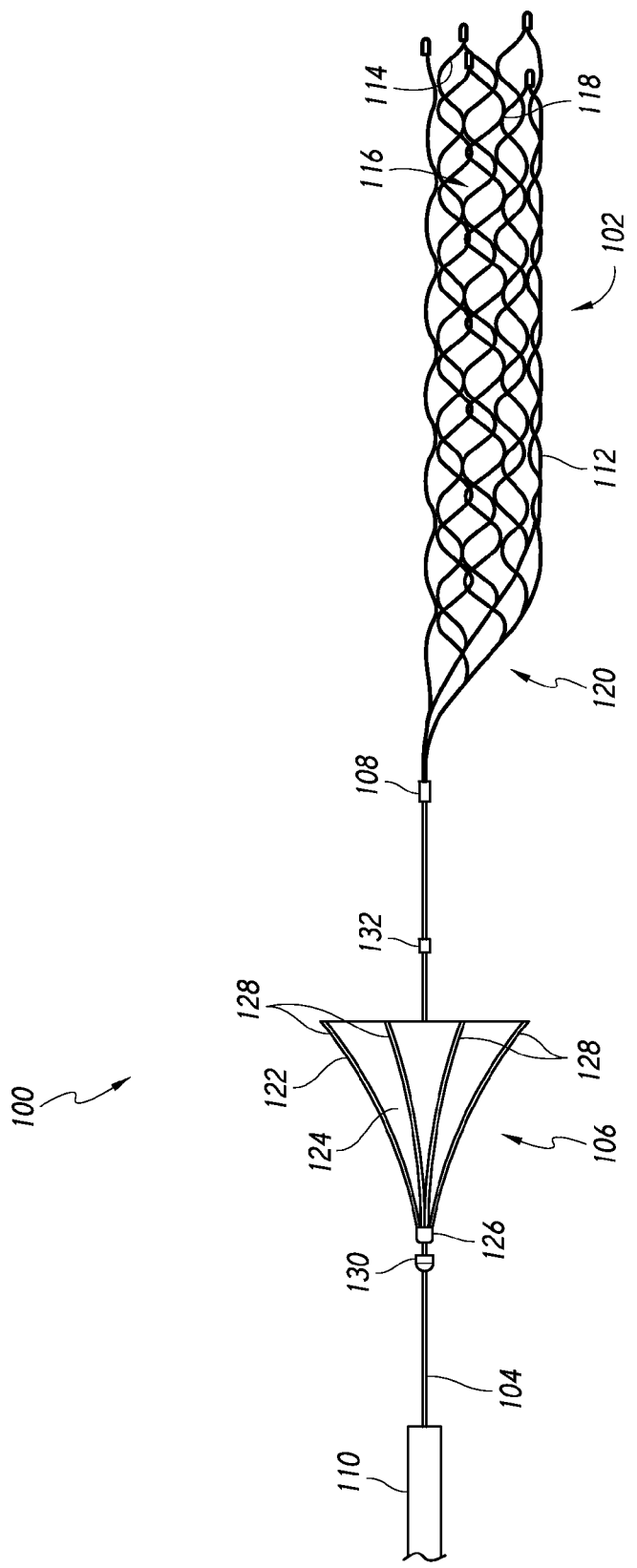
FIG. 1 illustrates a device, including a mechanical thrombectomy member and a flow-restricting apparatus, according to an embodiment.

FIG. 1 depicts a medical device 100 according to some embodiments of the subject technology. As illustrated in FIG. 1, the medical device 100 can comprise a mechanical thrombectomy apparatus 102, a manipulation member 104, and a flow-restricting apparatus 106. A proximal end portion of the mechanical thrombectomy apparatus 102 and a distal end portion of the manipulation member 104 can be joined at a connection 108. The flow-restricting apparatus 106 is also attached to the manipulation member 104, at a location proximal to the mechanical thrombectomy apparatus. The manipulation member 104 can extend through a catheter or microcatheter 110 such that an operator can manipulate the mechanical thrombectomy apparatus 102 and the flow-restricting apparatus 106, positioned within and/or distal to a distal end of the catheter 110, grasping the manipulation member 104 at a location proximal to a proximal end of the catheter 110.

The manipulation member 104 can have a length sufficient to extend from a location outside the patient's body through the vasculature to a treatment site within the patient's body. The manipulation member 104 can be monolithic or formed of multiple joined components. In some embodiments, the manipulation member 104 can comprise a combination of wire(s), coil(s), and/or tube(s). The manipulation member can have a substantially solid cross-section, meaning it does not comprise an internal lumen sufficiently large to permit operation of a separate apparatus therein or therethrough, but could comprise open space incident to the joining of multiple components. The manipulation member 104 can comprise one or more markers, e.g., comprised of radiopaque material(s) to aid radiographic visualization during manipulation.

The mechanical thrombectomy apparatus 102 and the manipulation member 104 can be substantially permanently attached together at the connection 108. That is, the mechanical thrombectomy apparatus 102 and the manipulation member 104 can be attached together in a manner that, under the expected use conditions of the medical device 100, the endovascular device and the manipulation member would not become unintentionally separated from one another.

Depending on the procedure and intended use of the medical device 100, it optionally may be advantageous to have a connection mechanism that permits intentional release of the medical device 100. In some embodiments, the medical device 100 can comprise a portion, located proximally or distally of the connection 108, that is configured for selective detachment of the endovascular device 102 from the manipulation member 104. For example, such a portion can comprise an electrolytically severable segment of the manipulation member. In some embodiments comprising a distal stop 132, a segment of the manipulation member between the distal stop 132 and the connection 128 can be configured for selective detachment. In some embodiments, the assembly 100 can be devoid of any feature that would permit selective detachment of the endovascular device 102 from the manipulation member 104.

Further details regarding connections that can be employed between the mechanical thrombectomy apparatus 102 and the manipulation member 104 disclosed in U.S. Pat. No. 7,300,458, entitled Medical Implant Having a Curable Matrix Structure, issued Nov. 27, 2007; U.S. Patent Application Publication No. 2011/0060212, entitled Methods and Apparatus for Flow Restoration, published on Mar. 10, 2011; U.S. Patent Application Publication No. 2012/0083868, entitled Methods and Apparatuses for Flow Restoration and Implanting Members in the Human Body, published on Apr. 5, 2012; U.S. Patent Application Publication No. 2011/0160763, entitled Blood Flow Restoration in Thrombus Management Methods, published on Jun. 30, 2011; U.S. patent application Ser. No. 13/834,945, entitled Connection of an Endovascular Intervention Device to a Manipulation Member, filed on Mar. 15, 2013, published as U.S. Patent Application Publication No. 2014/0194919 on Jul. 10, 2014; and U.S. patent application Ser. No. 13/835,130, entitled Connection of a Manipulation Member, Including a Bend without Substantial Surface Cracks, to an Endovascular Intervention Device, filed on Mar. 15, 2013, published as U.S. Patent Application Publication No. 2014/0194911 on Jul. 10, 2014; the entirety of each of which is hereby incorporated by reference herein.

The mechanical thrombectomy apparatus 102 can have a tubular or generally cylindrical shape in absence of external forces in some embodiments. The mechanical thrombectomy apparatus 102 can be self-expanding, e.g. by superelasticity or shape memory, or expandable in response to forces applied on the mechanical thrombectomy apparatus, e.g. by a balloon.

The mechanical thrombectomy apparatus 102 can comprise a frame 112 having a plurality of struts 114 and a plurality of cells 116 forming a mesh. The struts 114 can be connected to each other by joints 118. The frame can have a generally tubular or generally cylindrical shape with one or both of the proximal end and the distal end being open.

As illustrated in FIG. 1, a proximal portion 120 of the mechanical thrombectomy apparatus 102 can be tapered toward the proximal end. In some embodiments, the taper of the proximal portion can advantageously facilitate retraction and repositioning of the medical device 100 and mechanical thrombectomy apparatus 102. In some embodiments, the tapered proximal portion can also be designed to generally not contact the vessel wall during a blood flow restoration procedure, and to generally not interfere with the flow of blood within a vessel.

The mechanical thrombectomy apparatus 102 can be formed, for example, from cutting a sheet or a tube. When cut from a sheet, the mechanical thrombectomy apparatus 102 can be curled, rolled, or otherwise formed such that edges of the cut sheet overlap one another when the mechanical thrombectomy apparatus 102 is in a volume-reduced form. In some embodiments, the mechanical thrombectomy apparatus 102 is circumferentially continuous (e.g., forming a continuous cylindrical shape), lacking first and second edges and having no overlap or gap.

Regardless of whether the mechanical thrombectomy apparatus is circumferentially continuous, the mechanical thrombectomy apparatus 102 can have a central longitudinal axis both while in a volume-reduce form and when fully or partially expanded. In a volume-reduced form, the frame 102 of the mechanical thrombectomy apparatus 102 can have a smaller cross-sectional size to facilitate introduction of the mechanical thrombectomy apparatus 102 into and through the catheter 110. In some embodiments, the mechanical thrombectomy apparatus 102 can be self-expandable, and can expand toward a fully expanded configuration upon release from the catheter 110. Upon expansion, the mechanical thrombectomy apparatus 102 can expand towards an inner wall of a vessel, towards a thrombus occluding the inner wall of a vessel, or both.

The mechanical thrombectomy apparatus 102 can be manufactured in various lengths and relaxed-state diameters. In some embodiments, the mechanical thrombectomy apparatus 102 can have lengths, measured proximally to distally along the longitudinal axis, of 15 mm or less to 40 mm or more, though other ranges and sizes are also possible. The mechanical thrombectomy apparatus 102 can also have relaxed-state diameters, the diameters being measured when the mechanical thrombectomy apparatus 102 is fully free to expand, i.e., in absence of external forces. In some embodiments, the mechanical thrombectomy apparatus 102 can have a diameter of approximately 3 mm to 4 mm so as to be used in size 18 microcatheters (i.e. microcatheters with an inner diameter of approximately 0.21 inch). In some embodiments the mechanical thrombectomy apparatus 102 can have a diameter of approximately 5 mm to 6 mm so as to be used in size 27 microcatheters (i.e. microcatheters with an inner diameter of approximately 0.027 inch). Other ranges and values are also possible.

The cells 116 of the mechanical thrombectomy apparatus 102 can be configured to penetrate and engage a thrombus upon expansion of the mechanical thrombectomy apparatus into the thrombus, permitting retrieval of the thrombus by retraction of the mechanical thrombectomy apparatus.

Further details regarding expandable members, the manufacture of expandable members, and use of expandable members are disclosed in U.S. Pat. No. 7,300,458, entitled Medical Implant Having a Curable Matrix Structure, issued Nov. 27, 2007; U.S. Patent Application Publication No. 2011/0060212, entitled Methods and Apparatus for Flow Restoration, published on Mar. 10, 2011; U.S. Patent Application Publication No. 2012/0083868, entitled Methods and Apparatuses for Flow Restoration and Implanting Members in the Human Body, published on Apr. 5, 2012; U.S. Patent Application Publication No. 2011/0160763, entitled Blood Flow Restoration in Thrombus Management Methods, published on Jun. 30, 2011; U.S. patent application Ser. No. 13/834,945, entitled Connection of an Endovascular Intervention Device to a Manipulation Member, filed on Mar. 15, 2013, published as U.S. Patent Application Publication No. 2014/0194919 on Jul. 10, 2014; and U.S. patent application Ser. No. 13/835,130, entitled Connection of a Manipulation Member, Including a Bend without Substantial Surface Cracks, to an Endovascular Intervention Device, filed on Mar. 15, 2013, published as U.S. Patent Application Publication No. 2014/0194911 on Jul. 10, 2014; the entirety of each of which is hereby incorporated by reference herein.

As illustrated in FIG. 1, the flow-restricting apparatus 106 can comprise a frame 122 and a cover 124. The flow-restricting apparatus can be fixedly or slidably attached to the manipulation member 104. The flow-restricting apparatus can be fixedly attached to the manipulation member by, for example, soldering, welding, crimping, adhesive(s), or other joining method, or a combination thereof. When the flow-restricting apparatus is slidably attached to the manipulation member, the flow-restricting apparatus can axially slide proximally and distally along the manipulation member. Additionally or alternatively, the flow-restricting apparatus can slide rotationally about the manipulation member, permitting the flow-restricting apparatus to rotate about the manipulation member. Axial sliding of the flow-reducing apparatus can be limited by a proximal stop 130, a distal stop 132, or both.

The flow-restricting apparatus 106 has a collapsed configuration and an expanded configuration. In a collapsed configuration, the frame 122 can have a smaller cross-sectional size to facilitate introduction of the flow-restricting apparatus into and through the catheter 110. In some embodiments, the flow-restricting apparatus can be self-expandable, and can expand toward a fully expanded configuration upon release from the catheter 110. Upon expansion, the flow-restricting apparatus can expand towards an inner wall of a vessel and, in some embodiments, can abut the inner wall of a vessel.

The frame 122 can comprise a hub 126 and a plurality of struts 128. The hub 126 can comprises a passage 134 (FIGS. 2B and 6B) sized and shaped to accommodate the manipulation member 104, and can be circumferentially contiguous about the passage. Alternatively, the hub 126 can be circumferentially noncontiguous. The passage 134 can be larger than the manipulation member over a length of the manipulation member where the flow-restricting apparatus is attached (fixedly or slidably).

The hub 126 can have outer dimension(s) that are sufficiently small to permit the hub 126 to fit within a microcatheter, e.g., a size 18 microcatheter or a size 27 microcatheter.

The hub 126 has a length is sufficiently small to permit navigation of the flow-restricting apparatus through a microcatheter positioned in a tortuous vessel. For example, in some embodiments, the hub has a length less than 1 cm, less than 5 mm, or less than 3 mm.

The struts 128 are attached to the hub 126 and, when the flow-reducing apparatus 106 is in the expanded configuration, extend radially from the hub. The struts can be configured to support the cover 124, to restrict flow without a cover, or both. The struts can restrict flow without a cover by, for example, a dense arrangement of the struts, e.g., a porosity of 50%, 25%, or less.

FIGS. 2A-6B illustrate various embodiments of flow-restricting apparatuses, each comprising a frame 122 and a cover 124. FIGS. 2A-5 show frames 122 that comprise six struts 128. Each of these struts has a proximal end attached to the hub 126 and a free distal end. In some embodiments, frame 122 can have more or fewer than six struts. The flow-restricting apparatuses can have a flaring portion that extends radially (relative to a longitudinal axis) and distally from the hub and, optionally, a cylindrical portion extending distally from the flaring portion. The flaring portion can have various shapes in the expanded configuration. FIGS. 2A and 2B are a side view and an end view, respectively, of a flow-restricting apparatus with a frustoconical flaring portion. FIG. 3 is a side view of a flow-restricting apparatus with a hemispherical flaring portion. FIG. 4 is a side view of a flow-restricting apparatus with a hemiovoid flaring portion. FIG. 5 is a side view of a flow-restricting apparatus with a frustoconical flaring portion and a cylindrical portion.

FIGS. 6A and 6B illustrate a flow-restricting apparatus comprising a frame having 12 struts 128. Four proximal struts have a first end attached to the hub 126 and a second end attached to a pair of distal struts. Each of the pair of distal struts has a first end attached to one of the four proximal struts and a second end attached to another distal strut attached to another of the four proximal struts, as illustrated in FIG. 7. Alternatively, the second ends of the distal struts can be free (no directly attached to another strut), as illustrated in FIG. 8 for example. Portions 136 of the cover that are bounded by distal struts, but not proximal struts, optionally can be omitted in some embodiments.

In some embodiments, the frame can be made from single piece of material. For example, the frame can be cut from a tube or sheet, e.g., by laser cutting. In some embodiments, the frame can be made from multiple joined components. For example, the hub and struts can be formed separately, and thereafter attached together by soldering, welding, crimping, adhesive(s), or other joining method, or a combination thereof. In some embodiments, the frame can be made of super elastic metal, e.g., nickel titanium alloy, other metals, e.g., stainless steel, or a combination thereof. In some embodiments, the struts 128 can be woven or braided.

The all or a portion of the frame 122 can be configured as a flaring portion, for example as discussed above. A shape of the flaring portion in the expanded configuration can be heat set in some embodiments. For example, after the frame has been cut or assembled, the frame can be placed on a mandrel, then heated and subsequently cooled.

The cover 124 can be attached to an interior, exterior, or both of the frame 122. The cover can be a thin flexible membrane that includes or restricts flow therethrough. The cover can be made from one or more polymers such as, for example, PTFE, expanded PTFE, silicone, polyurethane, and thermoplastic rubbers such as CHRONOPRENE™, or from superelastic materials.

One or more markers comprising radiopaque material, e.g., platinum or gold, can be incorporated into the flow-restricting apparatus 106 in some embodiments. For example, a wire 138 of radiopaque material can be attached at or near distal end of the flow-restricting apparatus, for example, as illustrated in FIGS. 6A and 6B. As another example, one or more of the struts 138 can be coated with radiopaque material. In embodiments wherein the flow-restricting apparatus comprises one or more markers, particularly at the distal end of the flow-restricting apparatus, the marker(s) can provide indication of the position (e.g., along the manipulation member 104) and state (degree of collapse or expansion) of the flow-restricting apparatus on radiographic images.

The stops 130, 132 (FIG. 1) can be fixed to the manipulation member 104. For example, a stop can comprise a body having a central passage. The manipulation member can extend through the central passage, and the stop can be fixed to the manipulation member, e.g., by soldering, welding, crimping, adhesive(s), or other joining method, or a combination thereof. The stops have a shape and size that inhibit movement of the flow-restricting apparatus 106. A stop, e.g., the proximal stop 130, can have an outer dimension that is larger than an interior dimension of the hub 126 of the flow-restricting apparatus. A stop, e.g., the distal stop 132 can have an outer dimension that is slightly smaller than an interior dimension, e.g., an inner diameter, of the catheter 110, such that when the flow-restricting apparatus is an a collapsed configuration, distal movement of a distal end of the flow-restricting apparatus past the stop 132 is inhibited or prevented. The distal stop 132 can also be configured such that, when the flow-restricting apparatus is an expanded configuration, the distal stop 132 can move within the flow-restricting apparatus until abutting a portion of the flow-restricting apparatus near the proximal end of the flow-restricting apparatus, e.g., the hub 126. In some embodiments, the distal stop 132 and the connection 108 can be integrated together into a single structure. In some embodiments, the stops can be formed integrally with the manipulation member 104. In some embodiments, the stops can comprise radiopaque material, e.g., platinum or gold, and thereby function as markers.

Figure 9:
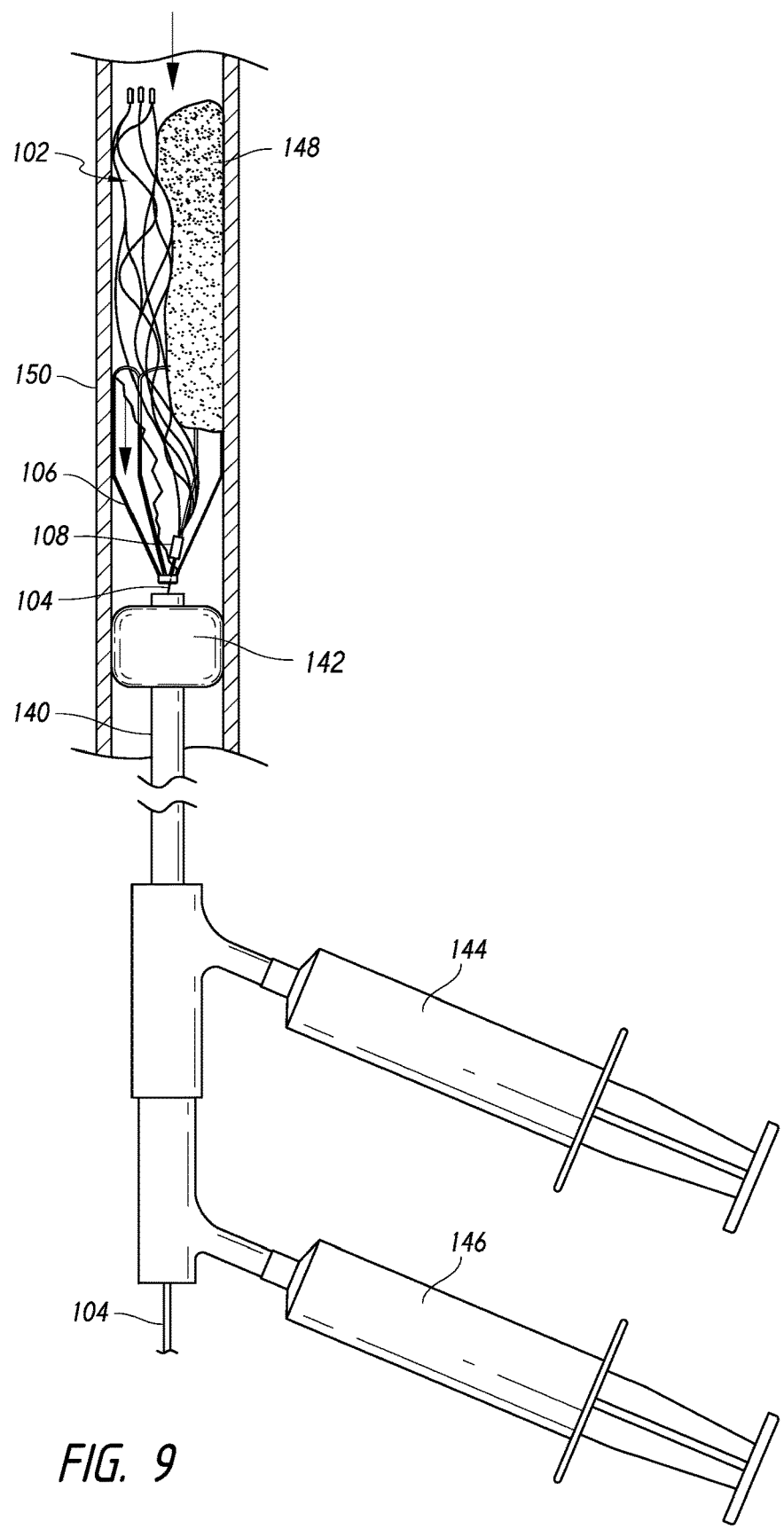
FIG. 9 schematically illustrates a system for blood flow restoration, thrombus removal, or both.

Referring to FIG. 9, the medical device 100 can be used in a system with a guide or retrieval catheter 140, which can comprise a balloon 142 in some embodiments. In embodiments that comprise a balloon catheter, the system can comprise a syringe 144 for expanding the balloon 142. Alternatively or additionally, the system can comprise a syringe 146 for applying aspiration. In some embodiments, both a balloon and an aspiration syringe may be omitted. Aspiration assistance can enable flow reversal to assist thrombus retrieval. Inflation of the balloon 142 can impede or prevent flow proximally through the vessel from the balloon 142 towards the mechanical thrombectomy apparatus 102. Continuous vigorous aspiration can be employed when the mechanical thrombectomy apparatus 102 is near a distal tip of the balloon guide catheter. In some embodiments, aspiration with flow reversal can help allow the distal vasculature to continue to have blood perfusing through the vessels during the retrieval process, and can inhibit the possibility of distal emboli. The aspiration with flow reversal can aid in the removal of thrombus by directing flow towards a lumen of the guide catheter 140 due to the aspiration. The mechanical thrombectomy apparatus 102 and thrombus 148 can thus be assisted by the flow to enter the lumen of the guide catheter 140. Use of the flow-restricting apparatus 106 can, in some embodiments, permit use of a balloon, aspiration, or both to be omitted, or shorten the duration of their use. In some embodiments, if withdrawal into the guide catheter 140 is difficult for any reason during aspiration, the balloon 142 can be deflated if present and inflated, and the guide catheter 140, catheter 110, the flow-restricting apparatus, and the mechanical thrombectomy apparatus 102 can be withdrawn simultaneously, while optionally maintaining aspiration.

Various techniques for removing a thrombus 148 will now be discussed with reference to FIGS. 10-18. These techniques can be performed with any of the embodiments of the medical device 100, flow-restricting apparatus 106, and mechanical thrombectomy device 102 disclosed herein, except as otherwise noted.

Figure 10:
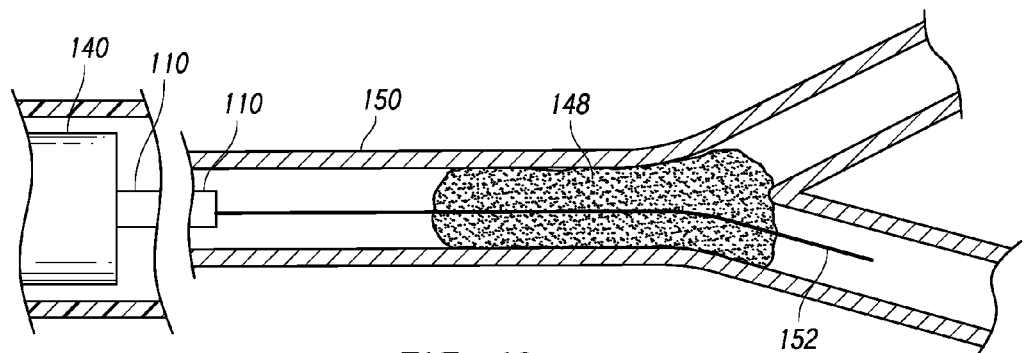
FIG. 10 illustrates a thrombus in a blood vessel.

FIG. 10 illustrates a thrombus 148 in an anatomical vessel 150. The medical device 100 may be inserted into an anatomical vessel 150 by first inserting a guide wire 152 into the anatomical vessel 150. The guide wire 152 can be advanced through a guide or retrieval catheter 140, which optionally includes a balloon near the guide catheter's distal end, and a catheter 110 to the treatment site, adjacent the thrombus 148. The guide wire 152 is advanced distally through the thrombus 148.

Figure 11:
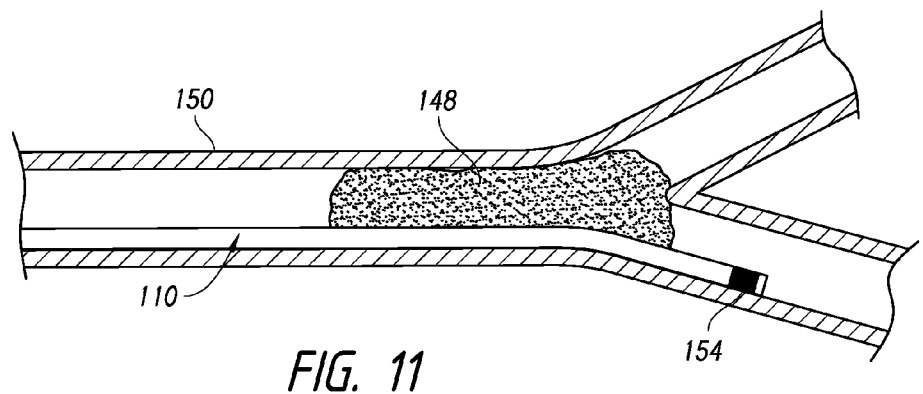
FIG. 11 illustrates a distal end of a microcatheter positioned distal to the thrombus.

Once the guide wire is in position, the catheter 110 is advanced over the guide wire 152, through a distal end of the guide catheter, into the anatomical vessel 150. Referring to FIG. 11, the catheter 110 is advanced distally through the thrombus 148 until a distal end 154 of the catheter 110 is positioned distal to the thrombus. The guide wire 152 is then withdrawn proximally.

Figure 12:
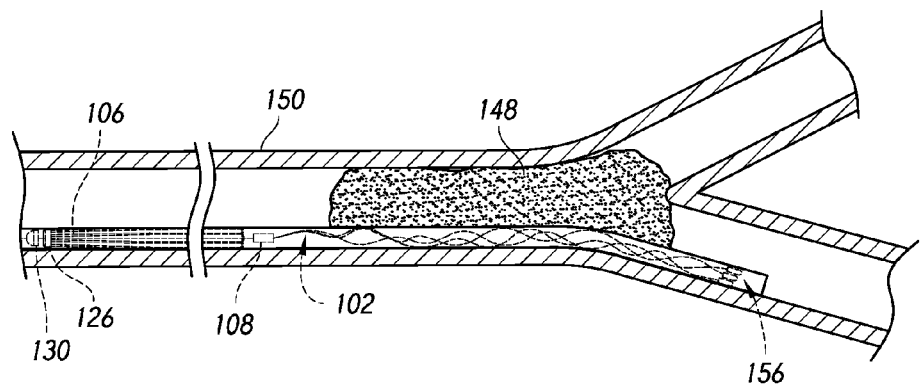
FIG. 12 illustrates a mechanical thrombectomy apparatus positioned in the microcatheter and spanning the thrombus, and a flow-restricting apparatus positioned proximal to the thrombectomy device in the microcatheter.

Referring to FIG. 12, the medical device 100 is advanced through the catheter 110 such that a distal end 156 of the mechanical thrombectomy apparatus 102 is disposed distal to the thrombus 148 in the anatomical vessel 150. The mechanical thrombectomy apparatus and the flow-restricting apparatus 106 are advanced through the catheter 110 by the manipulation member 104. In embodiments wherein the flow-restricting apparatus is slidably attached to the manipulation member, the proximal stop 132 abuts and pushes the hub 126 of the flow-restricting apparatus as the manipulation member is distally advanced. The catheter 110 compresses the mechanical thrombectomy apparatus 102 and the flow-restricting apparatus 106 and thus, maintains each of them in a compressed or volume-reduced configuration during advancement to the treatment site. In FIG. 12, the connection 108 is also configured as a distal stop, as discussed above.

Figure 13:
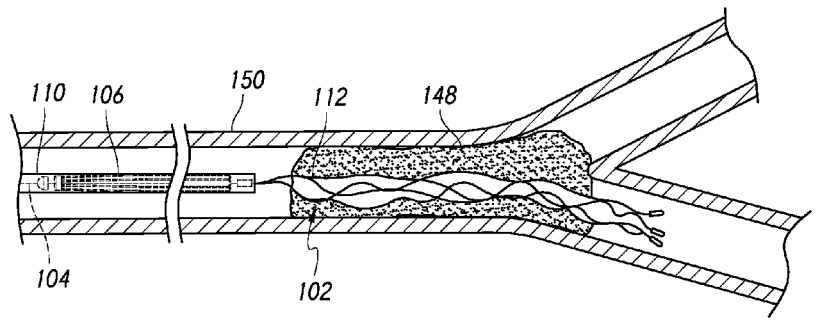
FIG. 13 illustrates the mechanical thrombectomy apparatus expanded into the thrombus, and the flow-restricting apparatus positioned within the microcatheter.

Referring to FIG. 13, the catheter 110 is withdrawn proximally relative to the mechanical thrombectomy apparatus 102 to expose the mechanical thrombectomy apparatus 102. If the mechanical thrombectomy apparatus is self-expanding, retraction of the catheter 110 can permit the mechanical thrombectomy apparatus 102 to expand. The frame 112 of the mechanical thrombectomy apparatus expands against a length of the thrombus 148 and engages the thrombus 148. A period of time can be allowed to pass to allow blood to reperfuse the downstream area, the mechanical thrombectomy apparatus 102 to penetrate the thrombus 148, or both. The flow-restricting apparatus 106 is retained within the catheter 110.

If necessary or desired, the catheter 110 can be advanced distally over the mechanical thrombectomy apparatus 102, while retracting, maintaining, or substantially maintaining the position of the manipulation member, to reposition or remove the mechanical thrombectomy apparatus. As the mechanical thrombectomy apparatus enters the catheter 110, a distal end of the flow-restricting apparatus 106 may abut the connection 108 (or the distal stop 132, shown for example in FIG. 1, if present separately from the connection 108) to push the flow-restricting apparatus proximally in the catheter 110.

Figure 14:
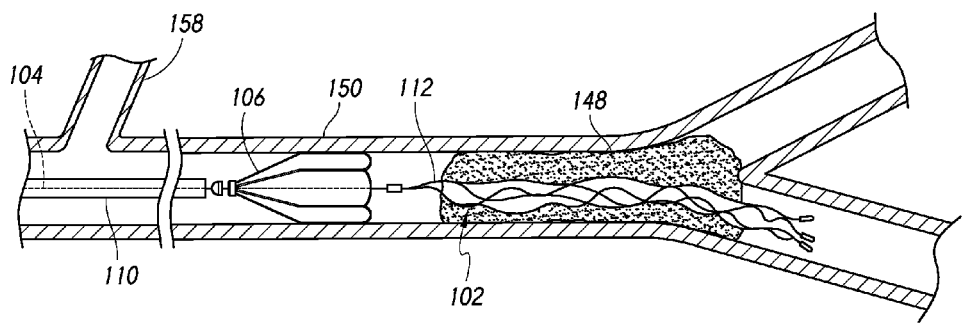
FIG. 14 illustrates the mechanical thrombectomy apparatus expanded into the thrombus, and the flow-restricting apparatus expanded in the vessel at a location proximal to the mechanical thrombectomy apparatus and thrombus.

Referring to FIG. 14, to expose the flow-restricting apparatus 106, the catheter 110 can be further retracted while maintaining or substantially maintaining the position of the manipulation member in the vessel, i.e., without advancing a proximal end of the manipulation member 104.

If the flow-restricting apparatus is self-expanding, retraction of the catheter 110 can permit the flow-restricting apparatus to expand at a location proximal to the mechanical thrombectomy apparatus 102. The frame 122 of the flow-restricting apparatus expands toward the wall of the anatomical vessel 150 and, if configured to do so, apposes the vessel wall. Expansion of the flow-restricting apparatus occludes, restricts, or otherwise diminishes blood flow in a distal direction. Because the flow-restricting apparatus is expanded in close proximity to the thrombus 148, blood is permitted to flow into any proximally diverging branch vessels 158.

Figure 15:
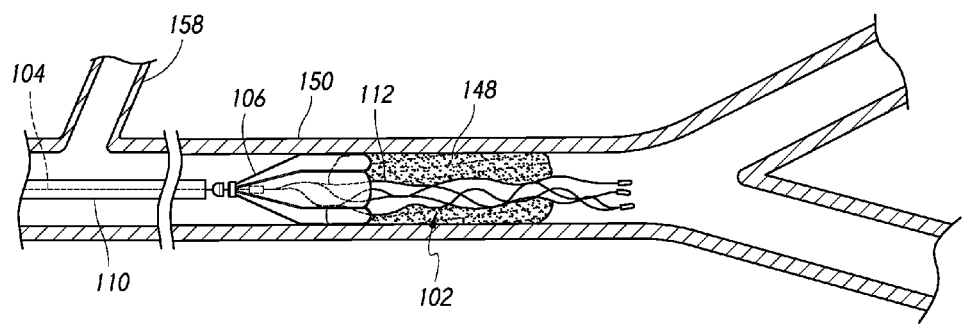
FIG. 15 illustrates the mechanical thrombectomy apparatus retracted into the flow-restricting apparatus.

Referring to FIG. 15, the mechanical thrombectomy apparatus 102 is withdrawn proximally, along with the thrombus 148. If the flow-restricting apparatus 106 is slidably attached to the manipulation member 104, retraction of the manipulation member can draw the mechanical thrombectomy apparatus and possibly some or all of the thrombus 148 into the flow-restricting apparatus. The mechanical thrombectomy apparatus can be retracted into the flow-restricting apparatus until the connection 108 (or the distal stop 132, shown for example in FIG. 1, if present separately from the connection 108) abuts an interior surface of the flow-restricting apparatus, e.g., the hub 126. Depending on the length of the flow-restricting apparatus and the position of the thrombus on the thrombectomy device, some or all of the thrombus may be positioned within the flow-restricting apparatus.

Figure 16:
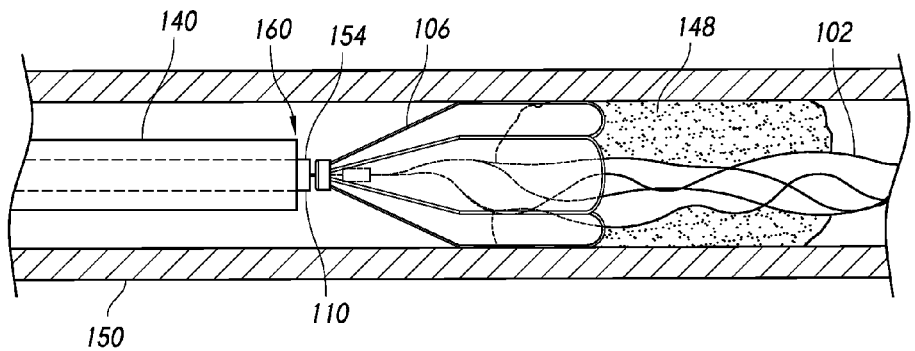
FIG. 16 illustrates the mechanical thrombectomy apparatus and the flow-restricting apparatus distal and proximate to a distal end of a retrieval catheter.
Figure 17:
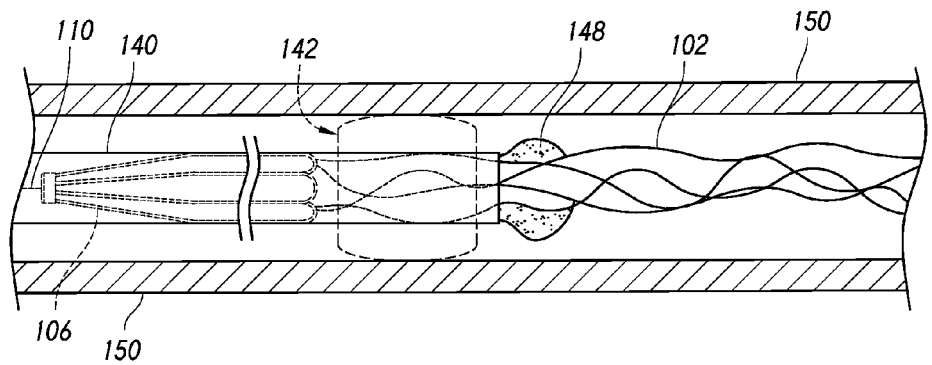
FIG. 17 illustrates the flow-restricting apparatus retracted into the retrieval catheter, and the mechanical thrombectomy apparatus and thrombus partially retracted into the retrieval catheter. A balloon on the retrieval catheter is shown in phantom indicating optional deployment.
Figure 18:
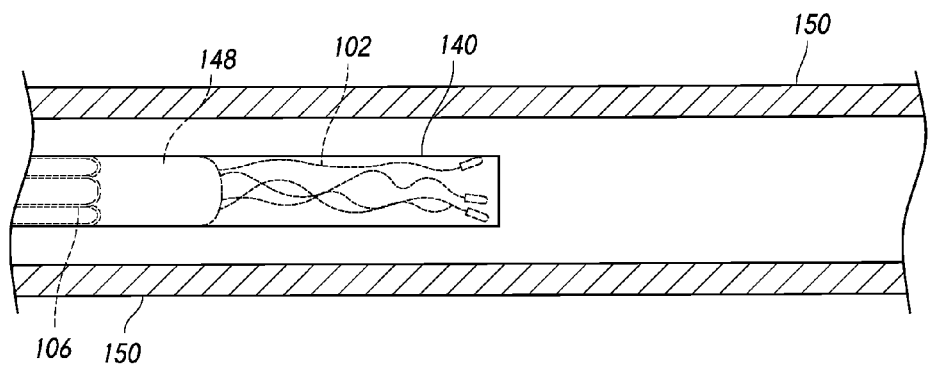
FIG. 18 illustrates the flow-restricting apparatus, the mechanical thrombectomy apparatus, and thrombus positioned entirely within the retrieval catheter.

Referring to FIGS. 16-18, the flow-restricting apparatus 106 and the mechanical thrombectomy apparatus 102 are withdrawn together (regardless of whether the flow-restricting apparatus is fixedly or slidably attached to the manipulation member) proximally toward the distal end 154 of the catheter 110, and then together with the catheter 110 toward the guide catheter 140 until the flow-restricting apparatus 106 is positioned immediately distal to the distal end 160 of the guide or retrieval catheter 140. Upon retraction into the guide catheter 140, the guide catheter causes the frame 122 of the flow-restoration apparatus and the frame 112 of the mechanical thrombectomy apparatus to collapse, with the engaged thrombus 148. The thrombus 148 is thus retrieved and removed from the anatomical vessel 150.

In some embodiments, the flow-restricting apparatus can be retracted slightly into the catheter 110 to clamp the flow-restricting apparatus onto the mechanical thrombectomy device, and possibly thrombus, depending on the size location of the thrombus on the mechanical thrombectomy device. In this way, the thrombus engagement can be increased, thereby improving the likelihood of successful thrombus retrieval. The flow-restricting apparatus can therefore assist with retrieving the thrombus, for example by containing at least a proximal portion of the thrombus and/or mechanical thrombectomy device, as the thrombus and/or mechanical thrombectomy device are moved proximally into the catheter 110 or guide or retrieval catheter 140.

Referring to FIG. 17, in embodiments wherein the guide catheter 140 comprises a balloon 142, the balloon optionally can be inflated to occlude flow during retraction of the flow-restricting apparatus 106 into the guide or retrieval catheter 140. Inflation of the balloon can inhibit or prevent an increase of distally directed blood flow upon retraction of the flow-restricting apparatus so that the flow does not oppose retraction of the thrombus 148 into the guide catheter. In some embodiments the balloon 142 is inflated, but is not inflated until the flow-restricting apparatus is within close proximity (e.g., 5 mm, 1 cm, 1.5 cm, 2 cm or 5-30 mm) of the distal end 160 of the guy retrieval catheter 140. In embodiments wherein an aspiration syringe 170 is attached to the guide or retrieval catheter 140, aspiration can be applied to aid thrombus retrieval before and/or after retraction of the flow-restricting apparatus into the guide or retrieval catheter 140. Use of the flow-restricting apparatus 106 can allow the duration of use of a balloon 142 or aspiration to be shortened, and possibly restricted to a final stage of thrombus removal after the flow-restricting apparatus has been collapsed. In this way, blood can be permitted to flow into vessels proximal to the thrombus 148 until the thrombus is drawn past those vessels. A balloon 142, aspiration, or both can be omitted in some embodiments. Omission of a balloon can allow the use of a guide or retrieval catheter 140 having a smaller diameter than a balloon catheter, allowing the guide or retrieval catheter to be advanced closer to the thrombus, improving the likelihood of successful thrombus retrieval and reducing the distance of the thrombus retraction for removal.

If retrieval of the mechanical thrombectomy apparatus 102 is determined to be undesirable, e.g., to avoid damaging the vessel 150, and the mechanical thrombectomy apparatus 102 is detachably connected to the manipulation member 104, the mechanical thrombectomy apparatus can be detached from the manipulation member 104 and can remain in the vessel 150.

Additionally, while the techniques for using the medical device 100 have been described above for blood flow restoration, the medical device 100 can also, or alternatively, be used with an implantable member (e.g., stent), such as the mechanical thrombectomy apparatus 102 or otherwise. For example, the implantable member can be released at a stenosis, aneurysm, or other appropriate location in a vessel to hold the vessel wall open and/or act as an occluding member.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. A method for retrieving thrombus from a blood vessel, the method comprising:
    advancing a distal end of a delivery catheter to the blood vessel;
    advancing a single elongate delivery member carrying a mechanical thrombectomy device and a flow-restricting device through the delivery catheter to the blood vessel with the flow-restricting device proximal to the thrombectomy device, the thrombectomy device having an open distal end and including a plurality of struts that comprise a plurality of free ends radially spaced apart from one another and surrounding an opening at the open distal end of the thrombectomy device, and wherein the elongate delivery member terminates distally at a location proximal of the open distal end of the thrombectomy device;
    expanding the thrombectomy device within the thrombus and capturing the thrombus with the thrombectomy device;
    expanding the flow-restricting device to at least partially occlude blood flow toward the thrombus;
    retracting at least a portion of the thrombectomy device and at least a portion of the captured thrombus into the flow-restricting device;
    retracting the flow-restricting device and the thrombectomy device into the delivery catheter.

2. The method of claim 1, further comprising inserting a guide wire through the thrombus, and advancing the distal end of the delivery catheter over the guide wire to the blood vessel.

3. The method of claim 1, wherein advancing the distal end of the delivery catheter to the blood vessel comprises advancing the distal end of the delivery catheter to within 3 cm of the thrombus.

4. The method of claim 1, wherein advancing the distal end of the delivery catheter to the blood vessel comprises advancing the distal end of the delivery catheter to a location distal to a distal end of the thrombus.

5. The method of claim 1, wherein advancing the single elongate delivery member comprises positioning the open distal end of the thrombectomy device distal to the thrombus and a proximal end of the thrombectomy device proximal to the thrombus.

6. The method of claim 1, wherein the flow-restricting device is maintained within the delivery catheter while expanding the thrombectomy device.

7. The method of claim 1, further comprising waiting for a period of at least 30 seconds after expanding of the thrombectomy device before expanding of the flow-restricting device.

8. The method of claim 1, wherein the flow-restricting device is expanded after expanding the thrombectomy device.

9. The method of claim 1, wherein retracting the at least a portion of the thrombectomy device into the flow-restricting device comprises retracting the thrombectomy device until a stop member abuts a portion of the flow-restricting device.

10. The method of claim 1, further comprising inflating a balloon on the delivery catheter.

11. The method of claim 10, further comprising inflating the balloon before retracting the flow-restricting device into the delivery catheter.

12. The method of claim 10, further comprising, before inflating the balloon, retracting the flow-restricting device with the thrombectomy device toward the delivery catheter until the flow-restricting device is within 1 cm of a distal end of the delivery catheter.

13. The method of claim 1, further comprising aspirating through the delivery catheter while retracting at least one of the thrombus, the flow-restricting device, or the thrombectomy device into the delivery catheter.

14. The method of claim 1, further comprising containing at least a portion of at least one of the thrombus and the thrombectomy device with the flow-restricting device while retracting the flow-restricting device and the thrombectomy device into the delivery catheter.

15. The thrombectomy device of claim 1, wherein each of the plurality of struts is a solid member.

16. The thrombectomy device of claim 1, wherein the plurality of struts define a generally cylindrical frame.

17. The thrombectomy device of claim 1, wherein the plurality of struts define a generally cylindrical frame, and wherein each of the plurality of struts is a solid member.

* * * * *